United States Patent [19]

Milosevic et al.

[11] Patent Number: 5,220,401
[45] Date of Patent: Jun. 15, 1993

[54] MULTIPLE INTERNAL REFLECTANCE LIQUID SAMPLING

[75] Inventors: Milan Milosevic, Fishkill; Nicolas J. Harrick, Ossining, both of N.Y.

[73] Assignee: Harrick Scientific Corp., Ossining, N.Y.

[21] Appl. No.: 888,841

[22] Filed: May 27, 1992

[51] Int. Cl.[5] .............................................. G01N 21/01
[52] U.S. Cl. .................................... 356/246; 356/244; 356/300
[58] Field of Search .................... 356/300, 244, 246

[56] References Cited

U.S. PATENT DOCUMENTS 3,370,502  2/1968  Wilks, Jr. .............................. 356/246
4,988,195  1/1991  Doyle ................................... 356/244

OTHER PUBLICATIONS

Doyle, *Applied Spectroscopy*, vol. 44, No. 1, Jan. 1990, pp. 50–59.

*Primary Examiner*—F. L. Evans

[57] ABSTRACT

A liquid cell for IRS comprising a rod-shaped crystal having a cylindrical sampling surface and integral conical end portions forming end entrance and exit faces for a radiation beam. The center of the end faces are masked. All radiation entering the entrance face internally reflects from the conical surface and propagates down the IRE by multiple internal reflections from the cylindrical sampling surface. The IRE can be sealed into a trough or flow-through housing for the liquid sample. The seals are at insensitive regions of the IRE.

10 Claims, 2 Drawing Sheets

5,220,401

MULTIPLE INTERNAL REFLECTANCE LIQUID SAMPLING

This invention relates to multiple internal reflection spectroscopy (IRS), and in particular to a novel accessory for the application of this analysis technique to the analysis of liquids.

BACKGROUND OF THIS INVENTION

Reference is made to a book authored by N. J. Harrick entitled "Internal Reflection Spectroscopy", published by Interscience Publishers in 1967. This book provides a complete description of the principles underlying this technology, and also describes the construction and configuration of so-called internal reflection elements (IREs) used in such analysis equipment. Attention is especially drawn to pages 223–227 which describes the application of IREs for use in liquid cells. Reference is further made to U.S. Pat. Nos. 4,730,882 and 4,602,869, which are also directed to different IRE and liquid cell geometries, the contents of which are hereby incorporated by reference.

In general, it is important to many companies that process liquids to be able to conduct in-line analysis or analyses of samples in the simplest and most economic manner. As is known, many conventional spectrometers generate a radiation beam which upon emerging from the instrument converges to a region in the so-called sampling space or compartment of the instrument, and if not intercepted or used will continue back into the instrument for detection and spectral analysis. It is common to locate the IRE element and transfer optics for the IRE element in an accessory in the sampling space so as to maintain the original focussing conditions. At the same time, it is desirable that the IRE element, which must physically contact the liquid, be suitably positioned for effective and efficient use.

The U.S. Pat. No. '869 referenced above describes a single reflection prism liquid cell for IRS. This construction offers limited interactions with the liquid sample and thus reduced signal-to-noise (S/N) ratios. A recent paper in Applied Spectroscopy, Vol. 44, No. 1, 1990, pps. 50–59, describes a cylindrical IRE cell using an IRE rod with a circular cross-section, which can be located in line with the optical beam in the sampling compartment. Disadvantages, however, of this construction include reduced light throughput due to the need for the entering and exiting beam to reflect off metallic surfaces, and the possibility of spurious spectra due to beam interaction with the seals for sealing the IRE rod within the cell.

SUMMARY OF INVENTION

One object of the invention is an IRE construction that is suitable for in-line analysis of liquids, providing increased S/N ratios and reduced spurious spectra.

Another object of the invention is an IRE and liquid sampling accessory for IRS using a cylindrical IRE which is simple to use while maintaining the original focussing conditions of the spectrometer.

There and other objects and advantages of the invention are achieved in accordance with one feature of the invention with a novel cylindrical IRE crystal that is configured with widening conical crystal ends integral with the cylindrical crystal rod. Preferably, the ends terminate in narrow cylindrical portions. The centers of the outside of both rod ends are masked off to block radiation.

In accordance with another feature of the invention, the crystal rod is mounted in a trough or flow-through cell such that liquid provided inside the cell wil contact all of the rod cylindrical surfaces except for the end cylindrical portions. The latter are used to support seals for sealing the IRE within the cell. When the cell is placed inside the sample compartment, the novel IRE allows entrance of the analyzing IRS radiation beam into the crystal via an annular region surrounding the center mask at one rod end. The entering beam totally internally reflects off of the conical surface, which redirects the beam to propagate down the rod via multiple internal reflections from its cylindrical major surface until it encounters the opposite conical end, from which it exits from the opposite rod end via a corresponding annular region after reflection from the conical surface. The exiting beam, modulated by interaction with a sampling in contact with the rod cylindrical surface, is re-aligned in the sampling compartment for ready detection and processing.

The advantages of the invention include: higher light throughput since all reflections are by total internal reflection except where the beam interacts with the sample; no spurious spectra due to beam interaction with the seals, as the seals can be located at insensitive edges of the IRE; increased sensitivity as a standard IRE length allows 10 reflections from the sample; very easy to use and align, as no other optics are necessary to transfer the beam and the sample need only be poured into the trough or flowed through the cell; and gives excellent spectra of any contacting liquid due to the multiple interactions of the beam with the liquid sample.

SUMMARY OF DRAWINGS

The invention will now be described in further detail with respect to several preferred embodiments, taken in conjunction with the accompanying drawings, wherein.

DETAILED DESCRIPTION OF PREFERRED EMBODIMENTS

Figure 1:
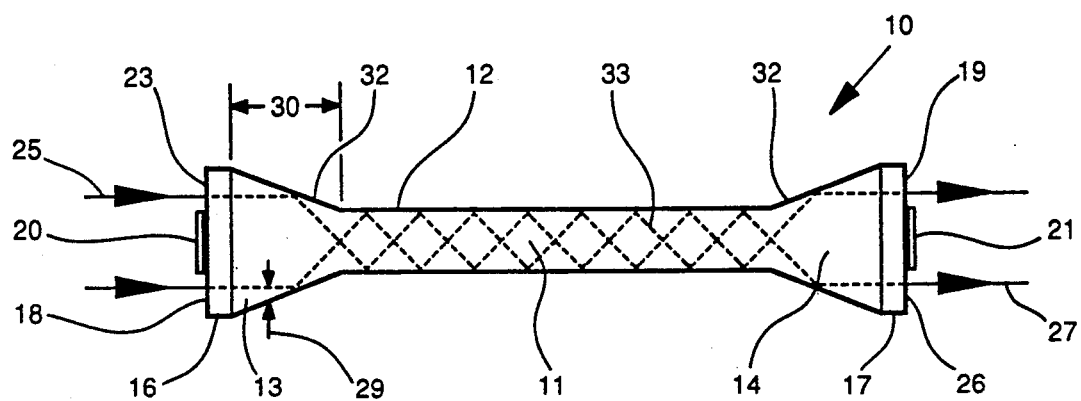
FIG. 1 is a side view of one form of IRE in accordance with the invention for direct immersion in a liquid sample to be analyzed.

FIG. 1 illustrates one form of an IRE in accordance with the invention for direct immersion into a liquid to be analyzed. The IRE 10 is a generally rod-like single crystal of one of the well-known IRE materials. It comprises a central section 11 having a circular cross-section forming a cylindrical sampling surface 12, which is optically polished in the usual way. Integral with the central section 11 are opposite end sections 13, 14, each of which are widening conical portions axially aligned with that of the central section 11. The end portions 13, 14 each terminate in a narrow cylindrical part 16, 17 forming transverse end faces 18, 19. Circular beam masks 20, 21 are placed at the center of each end face, forming at the left end face a narrow annular entrance window 23 for an axially incident radiation beam 25, and at the right end a correspondingly shaped annular exit window 26 for the exiting beam 27. The result of the masking is to form a hollow beam, but only the optical paths on one side are shown.

As will be clear, the size of the masks 20, 21 relative to that of the end faces, and the cone angle 29 and conical section length 30 are chosen such that all non-masked entering radiation internally reflects from the conical surface 32 and thus will propagate as shown at 33 by multiple internal reflections from the cylindrical sampling surface 12 before undergoing symmetrical redirection at the exiting end to form the exiting beam 27. No incident radiation passes through the IRE without reflecting from the sampling surface 12. Thus, all of the radiation will efficiently interact with the sample on the sampling surface.

As an example, which is not intended to be limiting, the IRE may have an overall length between end faces of 7.16 cm, a diameter of the cylindrical sampling surface 12 of 0.63 cm, a length 30 of each of the conical ends of 1.1 cm, a cone angle of 45° (which can vary between 30°-60°), a length of the narrow cylindrical end portions of 2 mm, and a mask diameter of 6 mm. The rod is symmetrical as shown. With these dimensions for a standard zinc selenide crystal material, an IR beam will undergo 10 reflections before exiting. With other IRE materials, the IRE can be given the same or different dimensions to achieve the optical performance described above.

In use, the IRE 10 is mounted inside a sealed trough-like cell structure (FIG. 2) or flow-through cell structure (FIG. 3) to form a liquid cell. The FIG. 2 cell 40 comprises a base member 41 for supporting the cell 40 in-line with the optical beam in the spectrometer sampling compartment. On the base 41 is mounted a generally cylindrical housing member comprising a central, section 42 to which are removably connected, as by screw threads, end sections 43, 44. The central section 42 has at its top an oval opening 45. The end sections 43, 44 each have outer projections 47 engaging an annular shoulder 48 on the central section, forming between the facing inner surfaces an annular seal area 50. In the seal area 50 is located an annular gasket 51 for supporting an O-ring 52 which sealingly engages the narrow cylindrical portions 16, 17 of the IRE 10. The end sections 43, 44 of the housing member each have bevelled openings 54 to accommodate a converging entering beam and a diverging exiting beam.

Figure 3:
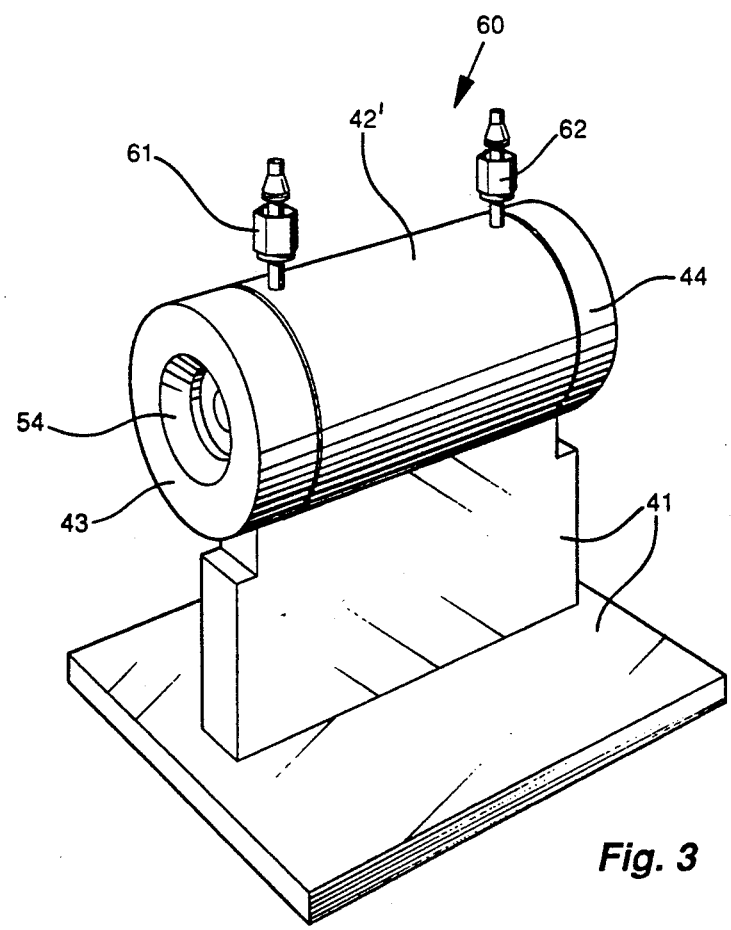
FIG. 3 is a view similar to FIG. 2 showing another form of liquid cell according to the invention.

The FIG. 3 flow-through cell 60 is similar, the same refernce numerals being used for similar parts. The only difference is the central section 42' which is without an opening, and the sample is supplied via standard fittings 61,62 to the cell interior. Both cell housing parts may be made up of stainless steel, and conventional gasket and O-ring materials may be used suitable for the liquid being analyzed.

Figure 2:
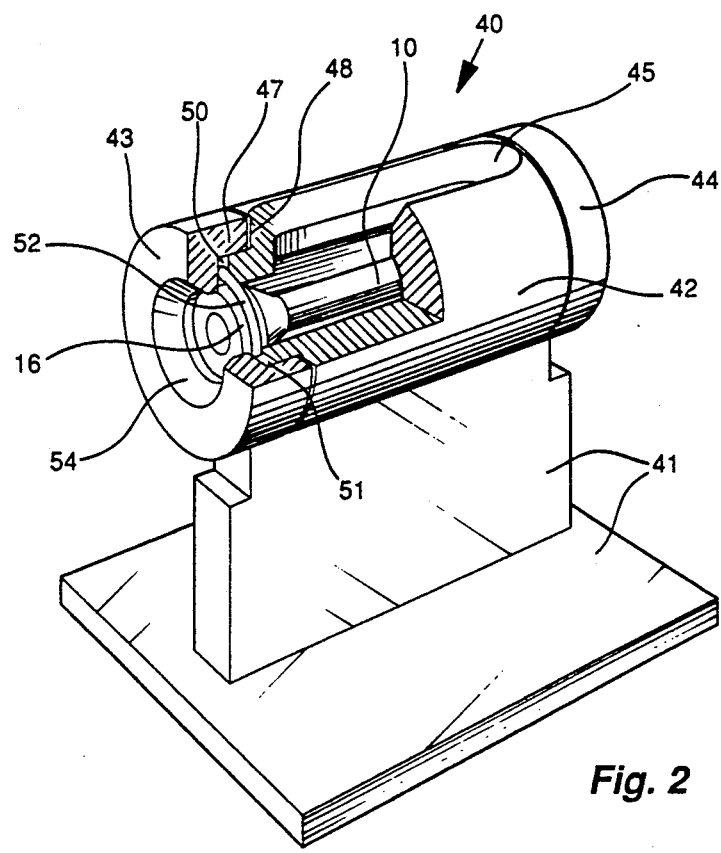
FIG. 2 is a perpective view of one form of liquid cell in accordance with the invention using the IRE of FIG. 1 for IRS analysis of a sample of a liquid, with part of the side being cut away to show the interior.

In use, the IRE 10 is placed within the respective cell housing 40, 60, the O-rings 52 installed, and the ends 43, 44 screwed on to form a sealed cell asembly. The trough cell in FIG. 2 is used by simply pouring the sample through the opening 45 so as to surround the IRE cylindrical sampling surface 12. The flow-through cell is used by simply flowing the liquid through the cell. The seals prevent leakage.

Figure 4:
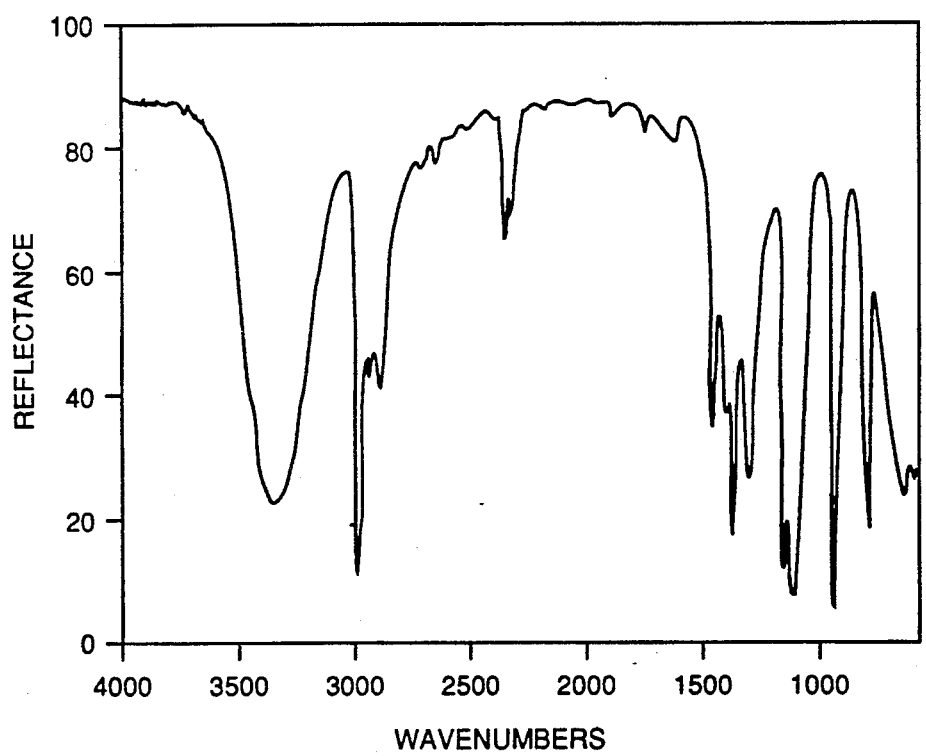
FIG. 4 is a sample spectra taken with the cell of FIG. 2.

FIG. 4 is a sample spectra of isopropanol taken with the FIG. 2 cell. The excellent spectra obtained will be evident.

As will be clear from FIGS. 1 and 2, the radiation does not reflect from the narrow cylindrical end regions 16, 17 where the seals are located. Those regions, being outside the radiation path, are insensitive thus eliminating O-ring spectral interference. Moreover, all reflections are total internal reflections (except at the sampling surface) so that no reflection losses are encountered. The result is higher sensitivity and better spectra. The ease of use is evident from the description.

It is also very easy to attach to the outside of the cell housing hoses or tubes leading to the spectrometer beam exit and entering ports, through which a purge medium is available. Thus, the entire beam path can easily be maintained in a purge atmosphere, as described in our copending application, Ser. No. 07/831,529, whose contents are hereby incorporated by reference, thus permitting easy sample exchanges while maintaining the purge atmosphere through the spectrometer and cell accessory.

The IREs of the invention can be constituted of any of the radiation transparent materials described in the Harrick book, and are useful with any of the radiations conventionally used in this field, including IR, UV and visible.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An internal reflection element (IRE) for use in internal reflection spectroscopy, said IRE comprising:
    a generally rod-shaped crystal having a central cylindrical first portion and generally conically-shaped second and third opposite end portions that widen outwardly from the central first portion,
    said crystal having at the end of the second portion an entrance surface for a radiation beam and at the end of the third portion an exit surface for the radiation beam,
    means for masking the entrance surface such that radiation incident orthogonally on the entrance surface will reflect off a conical surface before propagating through the central first portion by multiple internal reflections from its surface.

2. The IRE of claim 1, further comprising means for masking the exit surface such that radiation that did not multiply reflect from the surface of the central first portion will be blocked.

3. The IRE of claim 1, wherein the entrance and exit surfaces are transverse to the longitudinal axis of the rod-shaped crystal.

4. The IRE of claim 1, wherein the second and third end portions each have a terminating narrow cylindrical portion whose diameter exceeds that of the central portion.

5. The IRE of claim 1, wherein the central first portion has a polished outer cylindrical surface.

6. A liquid cell accessory for internal reflection speatroscopy (IRS), comprising:
    (a) an internal reflection element (IRE) comprising a generally rod-shaped crystal having a central cylindrical first portion and generally conically-shaped second and third opposite end portions that widen outwardly from the central first portion,
    said crystal having at the end of the second portion an entrance surface for a radiation beam and at the end of the third portion an exit surface for the radiation beam, means for masking the entrance surface such that radiation incident orthogonally on the entrance surface will reflect off a conical surface before propagating through the central first portion by multiple internal reflections from its surface, (b) a housing and means for supporting the IRE within the housing such that a liquid sample provided inside the housing will contact the outer surface of the IRE's central first portion.

7. The liquid cell of claim 6, further comprising said supporting means including liquid seals.

8. The liquid cell of claim 6, wherein said liquid seals are mounted at insensitive regions of the second and third end portions.

9. The liquid cell of claim 6, wherein said housing includes at the top an opening for receiving a liquid to be analyzed.

10. The liquid cell of claim 6, wherein said housing includes means for feeding through the housing a liquid to be analyzed.

* * * * *